United States Patent
Schinas et al.

(10) Patent No.: US 9,965,675 B2
(45) Date of Patent: May 8, 2018

(54) USING VIRTUAL REALITY FOR BEHAVIORAL ANALYSIS

(71) Applicants: Georgios P. Schinas, Salonika (GR); Ilias K Chrysovergis, Salonika (GR); Leontios J. Hadjileontiadis, Salonika (GR); Vasileios Baltatzis, Salonika (GR); Kyriaki-Margarita Bintsi, Edessa (GR)

(72) Inventors: Georgios P. Schinas, Salonika (GR); Ilias K Chrysovergis, Salonika (GR); Leontios J. Hadjileontiadis, Salonika (GR); Vasileios Baltatzis, Salonika (GR); Kyriaki-Margarita Bintsi, Edessa (GR)

( * ) Notice: Subject to any disclaimer, the term of this patent is extended or adjusted under 35 U.S.C. 154(b) by 9 days.

(21) Appl. No.: 15/266,583

(22) Filed: Sep. 15, 2016

(65) Prior Publication Data

US 2018/0075293 A1  Mar. 15, 2018

(51) Int. Cl.
| | |
|---|---|
| *G06K 9/00* | (2006.01) |
| *G06N 99/00* | (2010.01) |
| *G06T 19/00* | (2011.01) |
| *G06F 3/01* | (2006.01) |
| *G06K 9/42* | (2006.01) |
| *G06K 9/46* | (2006.01) |
| *G06K 9/62* | (2006.01) |
| *A61B 5/16* | (2006.01) |

(52) U.S. Cl.
CPC ............ *G06K 9/00335* (2013.01); *A61B 5/16* (2013.01); *G06F 3/011* (2013.01); *G06K 9/42* (2013.01); *G06K 9/46* (2013.01); *G06K 9/6228* (2013.01); *G06K 9/6269* (2013.01); *G06N 99/005* (2013.01); *G06T 19/006* (2013.01)

(58) Field of Classification Search
USPC ........................................................ 382/128
See application file for complete search history.

(56) References Cited

U.S. PATENT DOCUMENTS

2016/0140930 A1*  5/2016  Pusch ..................... G06F 3/011
345/633

* cited by examiner

*Primary Examiner* — Gregory F Cunningham

(57) ABSTRACT

Examples of the disclosure provide for calibrating a virtual reality environment based on data input in response to initial calibration prompts to provide a customized detection phase for a behavior analysis session. User interaction data are received during the customized detection phase and is dynamically pushed through a trained machine learning component to generate a dynamic behavior vector for the behavior analysis session, the dynamic behavior vector updating during the customized detection phase. The virtual reality environment is dynamically modified during the customized detection phase using the dynamic behavior vector.

20 Claims, 9 Drawing Sheets

USING VIRTUAL REALITY FOR BEHAVIORAL ANALYSIS

BACKGROUND

Childhood is an extremely sensitive period in human development, during which the brain, especially the circuitry governing emotion, attention, self-control, and stress, is shaped by the interplay of the child's genes and experiences. One of the unfortunate experiences that marks many childhoods is bullying. Bullying is a global social phenomenon that has existed in neighborhoods and schools for centuries and is still rising today. Bullying is defined as aggressive behavior that is persistent, intentional, and involves an imbalance of power or strength. It usually targets children and teenagers due to their lack of empathy, which is the capacity to understand or feel what another being is experiencing from within the other being's frame of reference, or the capacity to place oneself in another's position. Bullying can occur as verbal, physical, relational, or cyber-bullying.

The main roles identified in bullying includes the bully, the victim, and the bystander, with a negative impact on everyone involved. In particular, for the bullies, the consequences vary from violent behavior and anti-social personality disorder to educational problems, while the victims face anxiety, depression, lower self-confidence, and even self-harmful tendencies. The bystander tends to feel fearful and powerless to act, and guilty for not acting. One problem with bullying is the distinction in these roles—bully, victim, bystander—since a child may have multiple roles at various times. For example, a child may be the one subjected to bullying in one situation, while being the bully in another setting, depending on the social surroundings, which increases the difficulty in realizing effective intervention.

SUMMARY

Examples of the disclosure provide a system and method for gamified behavioral analysis. A virtual reality environment is calibrated based on data Input in response to initial calibration prompts to provide a customized detection phase for a behavior analysis session. User interaction data are received during the customized detection phase and is dynamically pushed through a trained machine learning component to generate a dynamic behavior vector for the behavior analysis session, the dynamic behavior vector updating during the customized detection phase. The virtual reality environment is dynamically modified during the customized detection phase using the dynamic behavior vector.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Corresponding reference characters indicate corresponding parts throughout the drawings.

DETAILED DESCRIPTION

Referring to the figures, examples of the disclosure provide a gamified behavioral analysis detection and intervention system within a virtual reality environment. This intelligent information and communication technologies (ICT)-based approach for bullying detection and intervention provides behavior self-management tools, set within a collaborative care context with professional psychological input, to enable a gamified behavioral analysis approach for capturing bullying tendencies and applying ICT-based interventions to counter identified risks based on low empathy, self-confidence, and awareness.

Additionally, the examples described herein enable customized behavioral analysis using virtual reality and machine learning to dynamically modify the user experience based on user interaction within the virtual environment. By dynamically modifying the behavioral analysis session in real-time based on user interaction, some examples reduce processing load and/or increase processing speed by strategically managing computational, processing, memory, and/or other resources. The effect of customizing the virtual reality experience to a user during a session, using automatically generated behavior vectors (e.g., provided by machine learning), improves performance of the application as well as the device hosting the application. Additionally, some examples may conserve memory, reduce network bandwidth usage, improve operating system resource allocation, and/or improve communication between computing devices by streamlining at least some operations, such as dynamic generation and modification of a gamified behavioral analysis session based on user interaction data during a detection phase, by automating at least some operations.

In some examples, the underlying common factor in the three roles identified in bullying—bully, victim, bystander—is behavior. Changes in behavior, due to the difference in a corresponding role, may be reflected in three basic characteristics of empathy, self-confidence, and awareness. Aspects of the disclosure capture these characteristics by combining behavioral information of a user dynamically acquired both from the real world and the virtual reality and augmented reality worlds, shaped by a gamified structure. This enables holistic support while obtaining personalized experience data for an individual user related to bullying stimuli.

Figure 1:
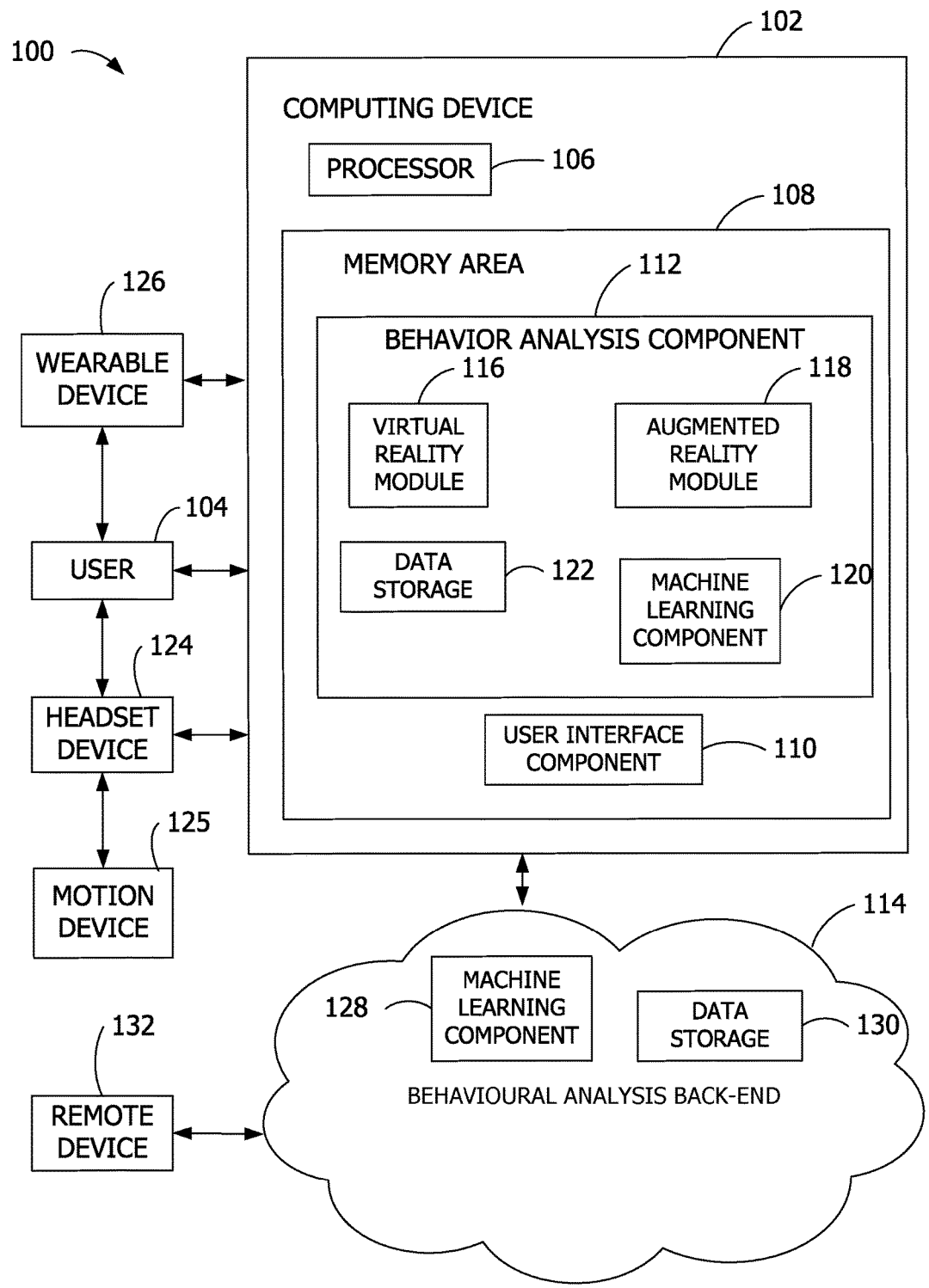
FIG. 1 is an exemplary block diagram illustrating a behavior analysis environment for gamified behavioral analysis using a trained machine learning component.

Referring again to FIG. 1, an exemplary block diagram illustrates a computing device for gamified behavior analysis in a behavioral analysis environment 100. In the example of FIG. 1, the computing device 102 associated with a user 104 represents a system for gamified behavior analysis. The computing device represents any device executing instructions (e.g., as application programs, operating system functionality, or both) to implement the operations and functionality as described herein. The computing device may include a mobile computing device or any other portable device. In some examples, the mobile computing device includes a mobile telephone, laptop, tablet, computing pad, netbook, gaming device, wearable device, and/or portable media player. The computing device may also include less portable devices such as desktop personal computers, kiosks, tabletop devices, industrial control devices, wireless charging stations, and electric automobile charging stations. Additionally, the computing device may represent a group of processing units or other computing devices.

In some examples, the computing device has at least one processor 106, a memory area 108, and at least one user interface component 110. The processor includes any quantity of processing units, and is programmed to execute computer-executable instructions for implementing aspects of the disclosure. The instructions may be performed by the processor or by multiple processors within the computing device, or performed by a processor external to the computing device. In some examples, the processor is programmed to execute instructions such as those illustrated in the figures (e.g., FIG. 3 and FIG. 4).

In some examples, the processor represents an implementation of analog techniques to perform the operations described herein. For example, the operations may be performed by an analog computing device and/or a digital computing device.

The computing device further has one or more computer readable media such as the memory area. The memory area includes any quantity of media associated with or accessible by the computing device. The memory area may be internal to the computing device (as shown in FIG. 1), external to the computing device (not shown), or both (not shown). In some examples, the memory area includes read-only memory and/or memory wired into an analog computing device.

The memory area stores, among other data, one or more applications. The applications, when executed by the processor, operate to perform functionality on the computing device. Exemplary applications include behavior analysis component 112, which may represent an application for gamified behavior analysis. The applications may communicate with counterpart applications or services such as web services accessible via a network (not shown). For example, the applications may represent downloaded client-side applications that correspond to server-side services executing in a cloud. In some examples, applications generated may be configured to communicate with data sources and other computing resources in a cloud during runtime, or may share and/or aggregate data between client-side services and cloud services. Behavioral analysis backend 114 may represent any type of data source accessible by computing device 102, whether at another computing device, in a cloud, at a network storage location, or any other suitable data storage location. In some examples, the memory area may store data sources, or a subset of data sources, which may represent data stored locally at memory area 108, such as data storage 122. In other examples, memory area 108 may store data access points associated with data stored remote from computing device 102 at data sources, or any combination of local and remote data.

The memory area further stores one or more computer-executable components. Exemplary components include user interface component 110. The user interface component, when executed by the processor 106 of computing device 102, cause the processor 106 to perform operations, including to receive user selections during user interaction with behavior analysis component 112, for example.

In some examples, the user interface component includes a graphics card for displaying data to the user and receiving data from the user. The user interface component may also include computer-executable instructions (e.g., a driver) for operating the graphics card. Further, the user interface component may include a display (e.g., a touch screen display or natural user interface) and/or computer-executable instructions (e.g., a driver) for operating the display. The user interface component may also include one or more of the following to provide data to the user or receive data from the user: speakers, a sound card, a camera, a microphone, a vibration motor, one or more accelerometers, a BLUETOOTH brand communication module, global positioning system (GPS) hardware, and a photoreceptive light sensor. For example, the user may input commands or manipulate data by moving the computing device in a particular way. In another example, the user may input commands or manipulate data by providing a gesture detectable by the user interface component, such as a touch or tap of a touch screen display or natural user interface.

Behavior analysis component 112 provides tools for gamified behavioral analysis using virtual reality. In some examples, behavior analysis component 112 includes virtual reality module 116, augmented reality module 118, machine learning component 120, and data storage 122. Virtual reality module 116 provides a virtual reality environment for user interaction during a gamified behavioral analysis session. Augmented reality module 118 provides an augmented reality environment for user reflection on stored behavioral analysis sessions. Machine learning component 120 provides a plurality of models for dynamic generation of behavioral vectors during gamified behavioral analysis sessions, providing the behavioral vectors to virtual reality module 116 for dynamic modification of the virtual reality environment during the session based on user interaction within the virtual environment.

Headset device 124 may be a wearable headset device communicatively coupled to computing device 102, through which user 104 interacts with behavior analysis component 112. For example, headset device 124 may provide the virtual reality environment generated by virtual reality module 116. Headset device 124 may also detect and/or capture user input data, such as response data, selection data, timing data, attention data, sensor data, and the like. Wearable device 126 may be a smartwatch, smart band, or other wearable configured to detect and/or capture biometric data and/or behavioral nature signals. Biometric data may include data such as pulse data, temperature data, galvanic skin response data, and the like. Behavioral nature signals may include gesture data, for example. Although wearable device 126 and headset device 124 are depicted as separate devices for illustrative purposes, aspects of the disclosure may provide for an integrated wearable device. In some examples, wearable device 126 and headset device 124 may be a single, integrated device having components that capture both biometric data and user input data. In still other examples, the capabilities of headset device 124 and wearable device 126 may be integrated with computing device 102, providing a wearable computing device implementing behavior analysis component. In one illustrative example, a motion detection or gesture detection device may be integrated with and/or affixed to a wearable headset to monitor hand gestures or hand movement, such as motion device 125, which may result in enhanced gameplay experience within the virtual reality environment provided by the behavioral analysis component 112. For example, a single hand palm rotation may enable a menu to appear, from which the user may be able to choose using the other hand.

Behavioral analysis back-end 114 may include machine learning component 128 and data storage 130. Machine learning component 128 may obtain stored behavior analysis sessions from data storage 130 and/or data storage 122, aggregate the session data, and perform cross-data analysis in order to refine the plurality of models implemented in machine learning component 120, for example. Additionally, telemetry data may be used by machine learning component 128 to train one or more models for behavioral analysis, such as behavior baseline models for calibration and behavior detection models for detection and analysis.

Figure 2:
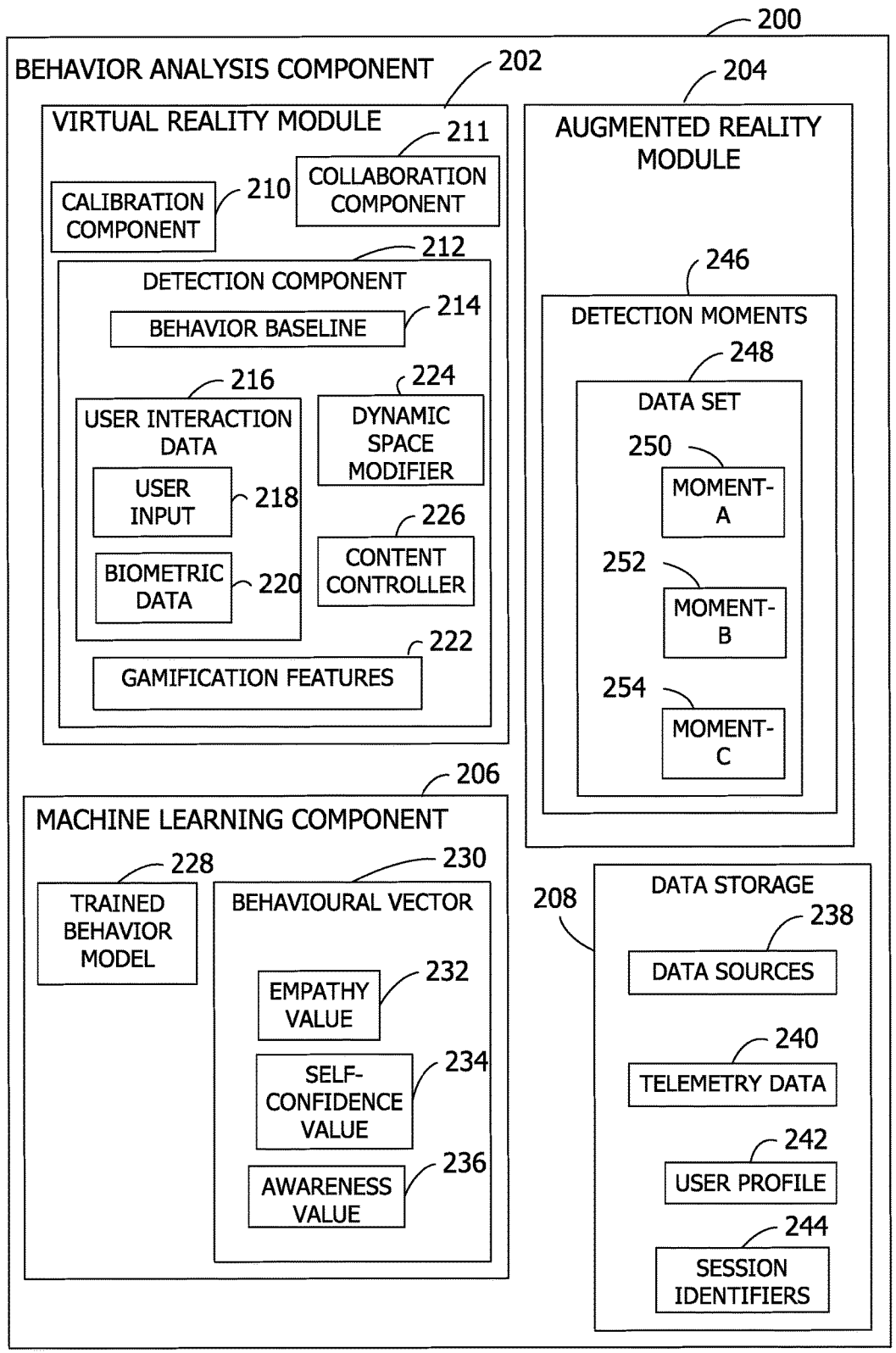
FIG. 2 is an exemplary block diagram illustrating a behavior analysis component.

FIG. 2 is an exemplary block diagram illustrating a behavior analysis component for gamified behavior analysis. Behavior analysis component 200 is an illustrative example of one implementation of behavior analysis component 112 in FIG. 1. Behavior analysis component 200 includes virtual reality module 202, augmented reality module 204, machine learning component 206, and data storage 208.

Virtual reality module 202 may include calibration component 210, collaboration component 211, and detection component 212. Calibration component 210 provides a calibration phase in a virtual reality environment to obtain user input to calibration prompts in order to determine a behavior baseline 214 for the behavioral analysis session. Calibration component 210 may push user input to the calibration prompts through machine learning component 206 to establish the behavior baseline, in some examples. In other examples, calibration component 210 may include a behavior baseline model that processes the user input to determine the behavior baseline for the behavior analysis session. The behavior baseline may be customized for a user associated with the behavior analysis session, such that the behavior baseline for an individual session is unique to the individual user and that individual session.

In some examples, collaboration component 211 is used for multiple-user or multiple-player sessions. Collaboration component 211 may interact with calibration component 210 to provide a calibration phase for individual players in a multi-player environment, in order to determine a behavior baseline for the individual players, customizing the behavior analysis session for the participants in a multi-player environment. In one illustrative example, this provides additional social perspective, such as for that of anti-bullying initiatives, to behavior analysis session results. During the calibration phase, virtual reality module 202 may use calibration component 210 and collaboration component 211 to calibrate the virtual reality environment to a plurality of users for a gamified multi-player behavioral analysis session.

Calibration component 210 provides behavior baseline 214 to detection component 212. Detection component 212 uses behavior baseline 214 to generate a detection phase for the gamified behavioral analysis session in virtual reality. During the detection phase, user interaction data 216 is dynamically received in real-time as a user, or multiple users, interacts with the virtual reality environment provided by virtual reality module 202. As used herein, dynamically refers to an automatic, continual, and/or iterative action that occurs in real-time. For example, throughout the duration of a behavioral analysis session provided by behavior analysis component 200, user input 218 is continually received in response to user interaction with the virtual reality environment provided. Biometric data 220 is also dynamically received during the detection phase, and processed concurrently with user input 218 on a continual basis using machine learning component 206.

Detection component 212 provides gamification features 222 as part of the virtual reality experience during the detection phase of the behavioral analysis session. Gamification features 222 may include elements that provide a user experience of participating in a game even as data and information is obtained through the user interaction with the game that enable behavior analysis. For example, goals, scores, measures, rewards, incentives, competition, recognition, unlocking levels, access requirements, and so forth, may serve as gamification features in a behavioral analysis session, which may engage and maintain user interest in the session.

Dynamic space modifier 224 dynamically modifies the virtual reality environment during the behavior analysis session in response to the user interaction data 216 obtained and processed by machine learning component 206. This dynamic modification of the virtual reality environment provides customization of individual behavior analysis sessions, such that an individual session experience may be unique to a user and that particular session, because it is modified and customized in real-time as the user interaction data are received. Content controller 226 may work with dynamic space modifier 224 to provide content, such as multi-media content for example, to the virtual reality environment during the session, and as the environment is dynamically customized.

Machine learning component 206 processes user interaction data 216 received during the detection phase provided by detection component 212 using one or more trained models, such as trained behavior model 228. Trained behavior model 228 may be trained using training data, such as behavioral data, questionnaires, psychological data, and the like. Trained behavior model 228 may also be updated based on previous behavioral analysis sessions provided by behavior analysis component 200, in some examples. Trained behavior model 228 receives user interaction data 216 and normalizes the data, removing noise and outliers. Trained behavior model 228 performs feature extraction on the normalized data, such as time analysis, frequency analysis, signal analysis, and the like to extract features from the normalized data. Feature selection is then performed on the extracted features and feature classification provided for the selected features using a machine learning algorithm. Trained behavior model 228 uses the classified features to generate behavioral vector 230, which may be a dynamic customized vector, such that the vector is dynamically updated as additional user interaction data are received during a given session for a given user.

Behavioral vector 230 may be a personalized behavioral vector of the user interacting with behavior analysis component 200 at a given time, and may be used to dynamically adjust the virtual reality space that follows in the session by providing the behavioral vector to the dynamic space modifier 224 of virtual reality module 202. In this way, the particularities of the reaction of each user become structural factors for the gamified virtual reality environment that follows during a behavioral analysis session. Behavioral vector 230 may include empathy value 232, self-confidence value 234, and awareness value 236, in this illustrative example.

As a user interacts with the gamified virtual reality environment during a behavioral analysis session, user interaction data are processed, the behavioral vector is dynamically generated, and the virtual reality experience is dynamically modified in response to the user interaction. For example, at a given point in the session, a user may be presented with content, and the user interaction data obtained in response to that content may determine the following content, routing the user through the gamified experience in a customized manner based on the user interaction in real-time.

Empathy value 232 may indicate a measure of empathy detected via user interaction in response to given content at a given point in the session. Self-confidence value 234 may indicate a measure of self-confidence detected via user interaction in response to given content at a given point in the session. Awareness value 236 may indicate a measure of awareness detected via user interaction in response to given content at a given point in the session. At any given point, for any given content, one or more of the values illustrated as part of behavioral vector 230 may be generated.

Data storage 208 may include data sources 238, telemetry data 240, user profile 242, and session identifier 244. In some examples, data storage 208 may be local to a computing device implementing behavior analysis component 200. In other examples, data storage 208 may be remote (not shown) from behavior analysis component 200. Data sources 238 may be a plurality of local or remote, or both local and remote, data sources. Data sources 238 may include data access points to data service providers, or data storage, or data access points to data stored remote from a computing device implementing behavior analysis component 200, in some examples Telemetry data 240 may include machine learning information derived from analysis of user interaction data and previous behavior analysis sessions stored at data storage 208. For example, telemetry data 240 may include information on how a given user with a specific behavior baseline responded to given content, user feedback, professional feedback, cross-data analysis, and the like. User profile 242 may include historical information corresponding to user interaction with behavior analysis component 200, as well as other user information. Session identifiers 244 may be unique identifiers associated with individual sessions that obfuscate identifying information of an associated user, such that cross-data analysis of multiple user sessions by a behavior analysis backend maintains privacy, confidentiality, and requisite healthcare related privacy regulations and requirements.

Augmented reality module 204 may access stored session data in data storage 208 in order to identify detection moments 246. Augmented reality module 204 may process stored session data from a behavior analysis session to identify moments during the session where user interaction indicated high levels of emotional engagement, based on behavioral modeling output from machine learning component 206. These moments may be identified as detection moments, and may include data set 248. Data set 248 may be a set of detection moments for a given session associated with a given user, for example. Data set 248 includes moment-A 250, moment-B 252, and moment-C 254. Augmented reality module 204 may select one or more of the moments from data set 248 to use in generating an augmented reality reflection point via a user computing device. For example, moment-A 250 may be a video clip of an interval of time during the behavior analysis session where user interaction data indicated the highest emotional engagement in relation to the remainder of the session. Augmented reality module 204 may superimpose the video clip of moment-A 250 to a real world experience via augmented reality using the user computing device, providing the user a reflection point on the experience in the virtual environment during the session and tying that reflection point into the real world experience as the user interacts with augmented reality module 204.

In these examples, after a virtual reality behavioral analysis session, augmented reality is employed to bring memories or moments from the virtual reality experience into the real world via augmented reality. This reflected information consolidates the virtual reality experience with the real world experience in a reflection process, reinforcing the behavioral model outputs. In this way, aspects of the disclosure foster the transmission of emotions and experiences from the virtual to the real world, providing a gaming experience that positively affects user behavior.

Figure 3:
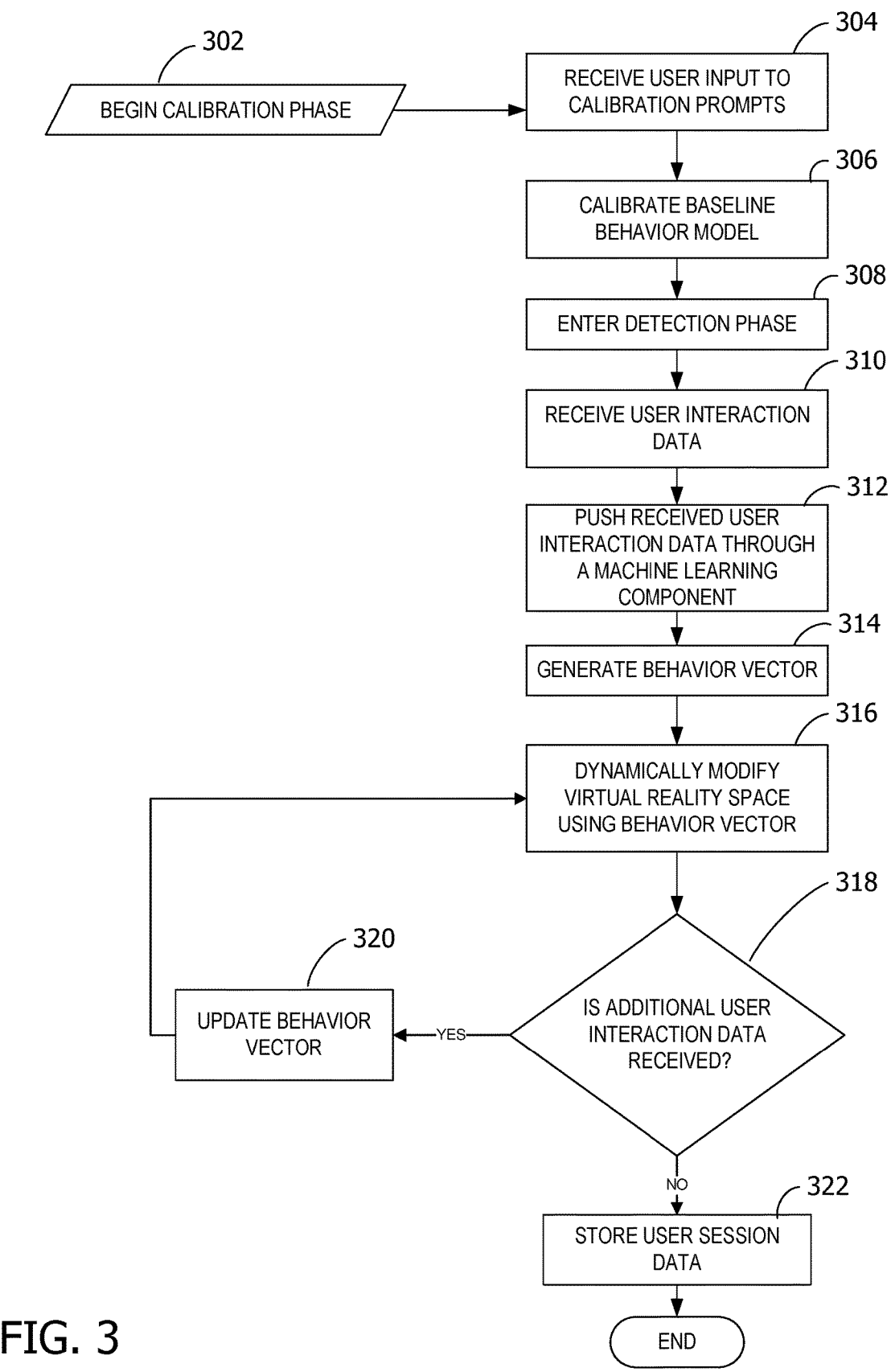
FIG. 3 is an exemplary flow chart illustrating operation of the computing device to generate a dynamic gamified behavior analysis session in a virtual reality environment.

FIG. 3 is an exemplary flow chart illustrating operation of the computing device to generate a dynamic gamified behavior analysis session in a virtual reality environment. One or more components described in FIG. 1 or FIG. 2 perform the exemplary operations described below.

The process begins with a calibration phase at operation 302. The calibration phase may provide calibration prompts configured to elicit user interaction that is used to establish a behavior baseline for an individual user and an individual session. For example, in the calibration phase virtual reality module 202 welcomes a user into the virtual reality environment or world and may provide an initial baseline interaction, such as an interaction with facial stimuli of Ekman's six basic emotions (e.g., faces expressing anger, disgust, fear, joy, sadness, and surprise). The initial calibration phase may present a gamification task prompting the user to correctly identify the displayed emotion represented by the faces presented. This may be used to categorize an initial behavior baseline, such as an emotional intelligence level, taking into account the activation of brain mirror neurons expressed via empathy detected based on user interaction. The calibration phase may also present a self-image of the user, a selfie, and prompt the user to select a level of his/her self-confidence. User selection during the calibration phase may be used in conjunction with other user interaction data, such as timing data (how long did it take the user to make the selection, how long did the user stare at his/her own face before making a self-confidence level selection, etc.) to evaluate the behavior baseline. In some examples, the behavior baseline may be an initial behavior vector provided by a machine learning component using a trained behavior model.

The process receives user input to calibration prompts at operation 304, calibrates a baseline behavior model at operation 306, and enters a detection phase at operation 308. The detection phase may provide the behavioral analysis session, routing the user through a virtual reality game environment based on user interaction, dynamically modifying and routing the user through the virtual reality space during the session. The process receives user interaction data at operation 310 and pushes the received user interaction data through a machine learning component at operation 312. The machine learning component may have one or more trained behavior models that process the received user interaction data to generate a behavior vector at operation 314. The behavior vector may be dynamic and may be used to dynamically modify the virtual reality space at operation 316. The generation of the behavior vector and the dynamic modification of the virtual reality space may be continually modified as user interaction data are received during a session.

The process determines whether additional user interaction data are received at operation 318. If a determination is made that additional user interaction data are received, the process updates the behavior vector at operation 320 and returns to operation 316. This process may iteratively repeat until a determination is made that no additional user interaction data are received, or alternatively when the session has concluded. The process then stores user session data at operation 322, with the process terminating thereafter.

Figure 4:
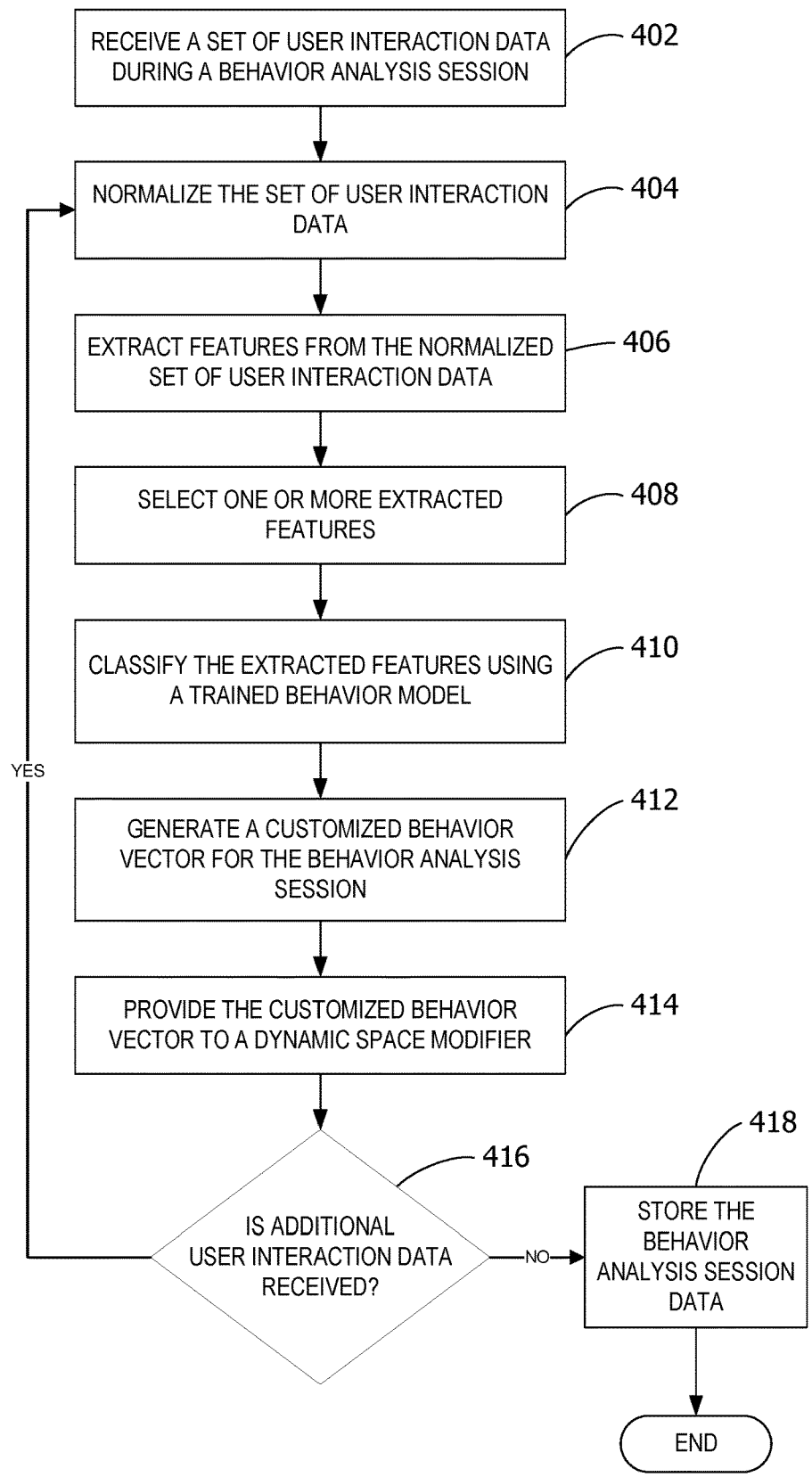
FIG. 4 is an exemplary flow chart illustrating operation of the computing device to customize the gamified behavior analysis session.

FIG. 4 is an exemplary flow chart illustrating operation of the computing device to customize the gamified behavior analysis session. The exemplary operations presented in FIG. 4 may be performed by one or more components described in FIG. 1 or FIG. 2, for example.

The process begins receiving a set of user interaction data during a behavior analysis session at operation 402. The set of data may be user input data, biometric data, sensor data, or the like. The user interaction data may be obtained via user interaction with a virtual reality environment. User interaction data may include, for example, without limitation, timing data, attention data, biometric data, selection data, response data, sensor data, and the like. Biometric data may include, for example, without limitation, heart rate or pulse data, temperature data, galvanic skin response data, stimuli response data, brain activity data (such as data obtained via electroencephalography), and the like. Sensor data may include, for example, without limitation, accelerometer data, gyroscopic data, gesture detection data, and the like.

The process normalizes the set of user interaction data at operation 404, and extracts features from the normalized set of user interaction data at operation 406. The process selects one or more extracted features at operation 408, and classifies the extracted features using a trained behavior model at operation 410. The process generates a customized behavior vector for the behavior analysis session at operation 412 and provides the customized behavior vector to a dynamic space modifier at operation 414.

The process determines if there is additional user interaction data at operation 416. If a determination is made that there is additional user interaction data, the process iteratively returns to operation 404. If a determination is made that there is no additional user interaction data, or alternatively is the session concludes, the process stores the behavior analysis session data at operation 418, with the process terminating thereafter.

Figure 5:
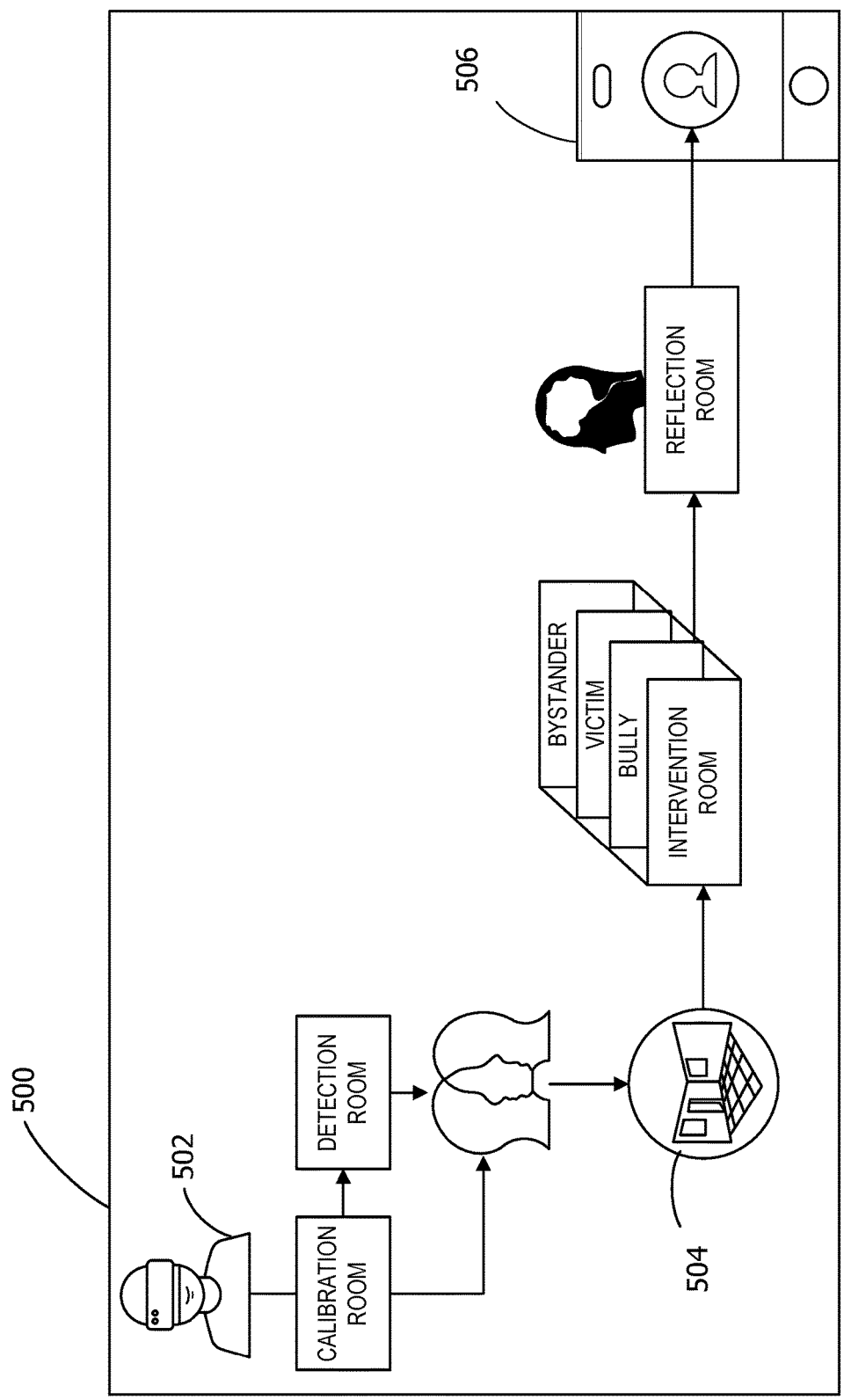
FIG. 5 is an exemplary diagram illustrating the architecture of gamified behavioral analysis using virtual reality.

FIG. 5 is an exemplary table illustrating the architecture of gamified behavioral analysis using virtual reality. Behavior analysis environment 500 may be an illustrative example of one embodiment of behavioral analysis environment 100 in FIG. 1.

User 502 may interact with a gamified behavioral analysis session in virtual reality space 504 using a wearable device. The output of the behavioral model, the machine learning component, of the behavior analysis system affects the structural characteristics of the virtual reality world used in the intervention model and the reflection model of the behavioral analysis session. The system calibrates the session and the virtual reality space in a calibration room of virtual reality space 504, then moves a user into a detection room calibrated for user 502. The system dynamically adjusts to the individual characteristics of the user for a given session, providing a dynamically modified virtual reality space that changes and becomes personalized according to the behavioral vector of the user as the user interacts with the system in the intervention room. The intervention room may provide concepts or scenarios associated with different roles, such as bully, victim, and bystander in one example. The content in the virtual reality space is formed with the relevant multi-media and/or audiovisual content that, based on neuroscience and stored behavioral data, will positively impact the user as the user engages with the virtual reality during the session.

A reflection room may be provided during or following a session, where user interaction and behavioral analysis feedback or results provide reflection points to emphasize the emotional experience and reaction of user 502 to the content present in virtual reality space 504 during the session. Reflection points may also be further provided by an augmented reality component of the behavior analysis component via user device 506, using positive moments from the session as part of an augmented reality experience aimed at positively affecting the behavior associated with user 502, such as by increasing empathy, self-confidence, and awareness.

Aspects of the disclosure enable emotional engagement for a user in a game-parameter that controls the navigation within the virtual reality space. When the user inside the corresponding virtual reality space views content associated with a specific behavioral impact (i.e. anti-bullying), user interaction data indicating emotional engagement with the content unlocks the next step or level in the gamified session. This may be controlled by the trained behavioral model that dynamically outputs the current behavioral vector—the level of empathy, self-confidence, and/or awareness—in response to the content being presented. Concurrently, gamification features, such as the completion of tasks, collecting points, the completion of achievements, and so forth, render the behavioral analysis session useful, effective, and entertaining, further engaging the user.

In one illustrative embodiment, a user may interact with the virtual environment via a wearable headset device communicatively coupled to another wearable device. In this example, the other wearable device may be a smart watch or band that detects biometric data. The other wearable device may include sensors, such as a gyroscope, that provide for control in the virtual environment provided by the headset device, for example by turning a wrist wearing the device to move forward through the virtual reality space provided via the headset device.

Figure 6:
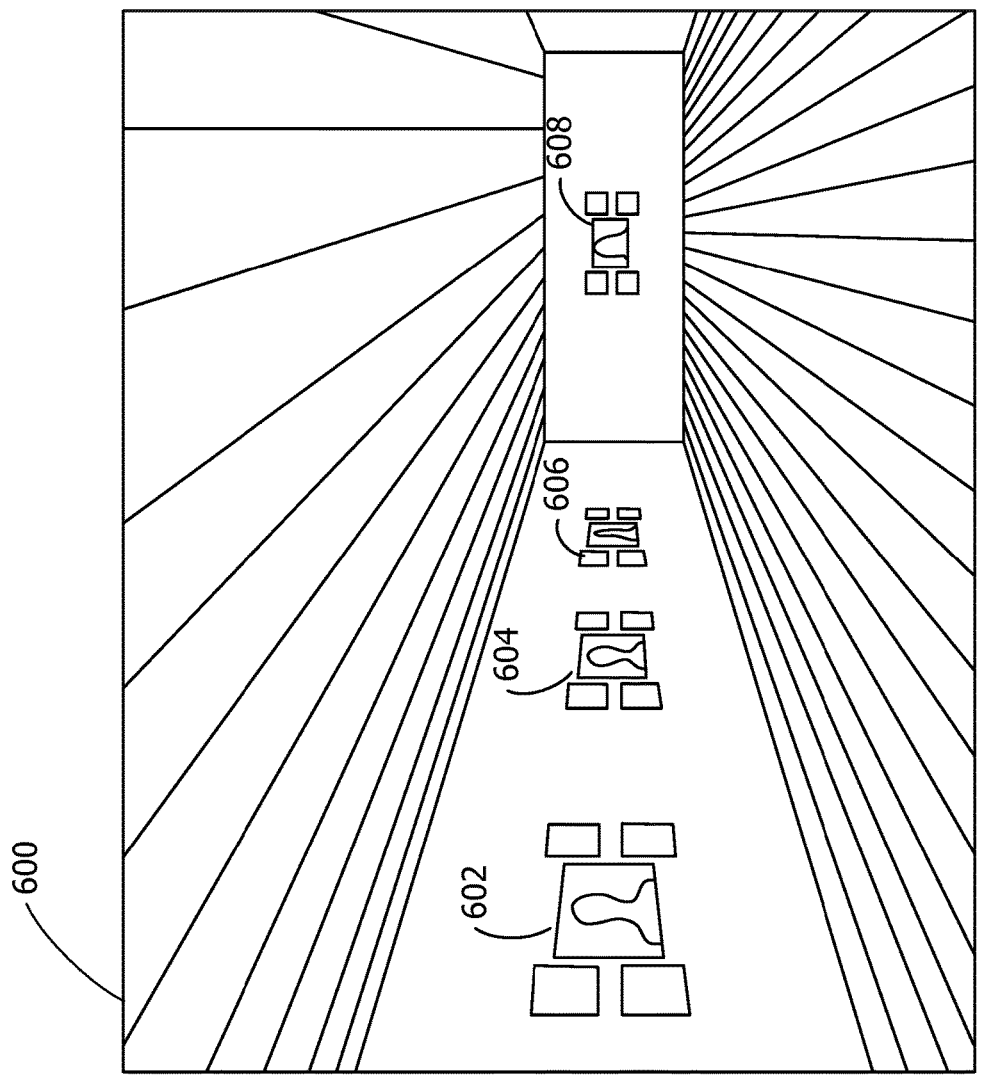
FIG. 6 is an exemplary diagram illustrating a user Interface of a gamified behavior analysis session using virtual reality.

FIG. 6 is an exemplary diagram illustrating a user interface of a gamified behavior analysis session using virtual reality. User interface 600 may be an illustrative example of one embodiment of a virtual reality environment provided by virtual reality module 116 in FIG. 1.

User interface 600 represents a virtual user interface that may, in some examples, provide for user interaction within a virtual reality space using a wearable headset device. User interface 600 represents an example of a calibration phase or calibration room of virtual reality module, provided by a calibration component of the system, such as calibration component 210 in FIG. 2. In this illustrative example, a user may be presented with facial stimuli of Ekman's six basic emotions (e.g., faces expressing anger, disgust, fear, joy, sadness, and surprise). The initial calibration phase may present a gamification task prompting the user to correctly identify the displayed emotion represented by the faces presented. In this example, a user may virtually walk through the calibration room presented in user interface 600, stopping in front of image 602 and selecting an emotion that the user corresponds with the image, moving on to image 604 within the virtual calibration room, selecting an emotion that corresponds with image 604, and on to image 606 and image 608 for selection.

These user selections or interactions within the virtual calibration room may be used to categorize an initial behavior baseline, such as an emotional intelligence level, taking into account the activation of brain mirror neurons expressed via empathy detected based on user interaction. The calibration phase may also present a self-image of the user, a selfie, and prompt the user to select a level of his/her self-confidence. For example, image 608 may be a reflective image, or a self-image of the user. User selection during the calibration phase may be used in conjunction with other user interaction data, such as timing data (how long did it take the user to make the selection, how long did the user stare at his/her own face before making a self-confidence level selection, etc.) to evaluate the behavior baseline. In some examples, the behavior baseline may be an initial behavior vector provided by a machine learning component using a trained behavior model.

The user interaction data captured during the calibration phase, as a user interacts with the virtual calibration room, calibrates a baseline behavior model for a detection phase of the behavioral analysis session, discussed below.

Figure 7B:
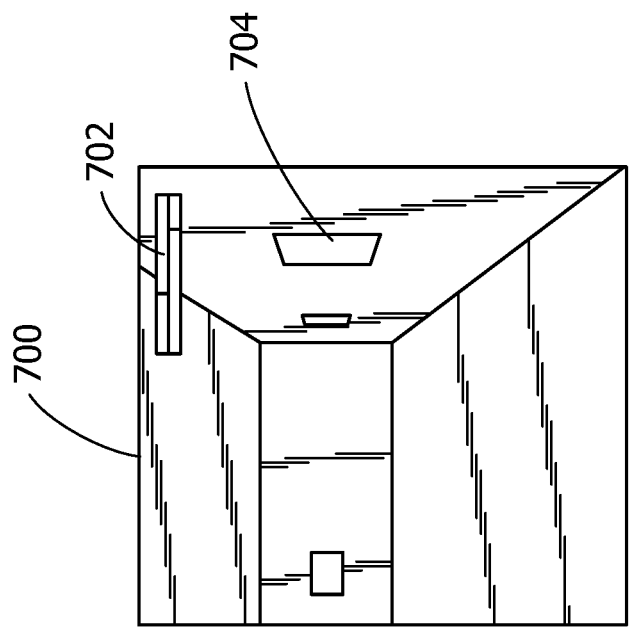
FIGS. 7A & 7B are exemplary diagrams illustrating a user interface of a gamified behavior analysis session dynamically adapting based on user interaction using virtual reality.
Figure 7A:
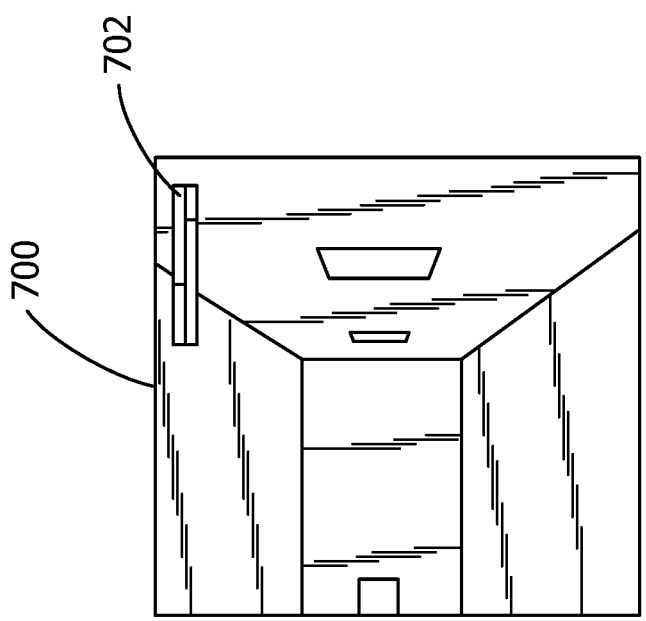

FIGS. 7A & 7B are exemplary diagrams illustrating a user interface of a gamified behavior analysis session dynamically adapting based on user interaction using virtual reality. FIGS. 7A & 7B may be an illustrative example of a detection phase following a calibration phase of a behavioral analysis session using virtual reality.

User interface 700 represents a virtual user interface that may, in some examples, provide for user interaction within a virtual reality space using a wearable headset device. User interface 700 represents an example of a detection phase or detection room of virtual reality module, provided by a detection component of the system, such as detection component 212 in FIG. 2.

Gamification element 702 may be an illustrative example of one type of gamification element used by virtual reality module 202 in FIG. 2 to route the user through a virtual reality game environment and drive user interaction. In this example, gamification element 702 is represented as a sliding bar depicting two different measurements, which may be displayed as two different colored bars in some examples. For example, the top sliding bar element may be a yellow bar that reflects empathy levels detected by the system, while the bottom sliding bar element may be a red bar that reflects self-confidence levels detected by the system based on user interaction in the virtual reality environment. As the user is routed through the virtual environment during a detection phase, the system dynamically modifies and routes the user through the virtual reality space based on user interaction and the behavior vector, which may be reflected by levels detected and measured in the illustrative gamification element 702, for example.

In this illustrative example, empathy levels detected and reflected in gamification element 702 may provide an inactive room or space in the virtual environment that is activated by a change in the detected empathy level of the user, with the activation of the new room or space indicated by modification 704 to the environment, depicted as a spotlight turning on in the now-active room in this example. The virtual reality space may be continually modified as user interaction data are received during a session, guiding a user through the virtual reality environment and routing the user through the behavioral analysis session based on the user interaction with the virtual reality content presented.

Figure 8:
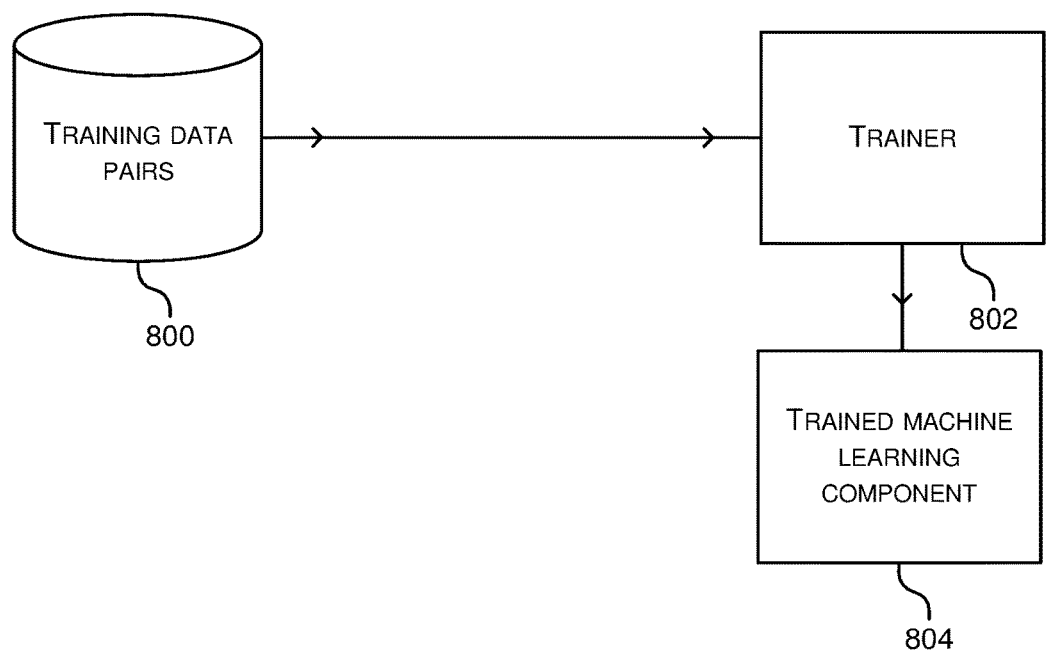
FIG. 8 is a schematic diagram of how to create a trained machine learning component, such as that of FIG. 1.

FIG. 8 is a schematic diagram of how to create a trained machine learning component, such as that of FIG. 1. Millions of training data pairs (or more) may be stored at a database 800 or other storage locations. In some examples, a training data pair comprises a content item, such as an image or multi-media file, and a corresponding ground truth behavioral data. In other examples, for the training of the machine learning component, training data may comprise the given answers to one or more behavioral analysis tests, as well as user answers to one or more questionnaires completed both before and after use of the behavioral analysis application. An individual user's biometric data captured during interaction with the system during a behavioral analysis session may be compared to the individual's own biometrics reference, which is calculated at the calibration stage, and used by the trained machine learning component to calculate and/or identify a behavioral vector for that individual user and session.

A trainer 802 accesses the training data pairs 800 and uses them to train and produce a trained machine learning component 804 such as a random decision forest, a convolutional neural network, a support vector machine, or other trained regressor or classifier, for example. The resulting trained machine learning component 804 may then be used as described above with respect to FIGS. 1-4. The type of training data used to train the machine learning component corresponds with the type of data input to the machine learning component at test time. Test time is the time in which the machine learning component is operational to compute behavioral vectors from previously unseen raw biometric and behavioral data. By using a wide variety of training data examples performance of the trained machine learning system is improved both in terms of accuracy and in terms of ability to generalize to examples which are different from the training examples.

Additional Examples

In some examples, aspects of the disclosure may be realized via the use of a smartphone or mobile computing device affixed or communicatively coupled to a virtual reality headset (e.g. HOMIDO®, Google Cardboard™). The calibration module welcomes the user into the virtual reality world, such as via a digital assistant using a natural language interface. The user may be asked to interact with a baseline calibration test to establish the Initial behavior model for the session. The user's emotional and self-confidence choices, the time spent making the response, and the routing with the virtual reality world are continuously captured by aspects of the disclosure. In addition, biometric data, such as heart rate, skin temperature, galvanic skin resistance, and so forth, are registered with user of another wearable, such as MICROSOFT® Band in some examples. In this example, a sense of coexistence of both real world and virtual reality environments may be provided, using an accelerometer of the wearable device as a course navigator, such as by twisting a wrist wearing the wearable (i.e. counter-clockwise for backwards, clockwise for forwards, etc.). Following a calibration phase, a detection phase may begin that provides emotionally targeted content, such as content related to bullying. For example, the bullying content may be categorized into three levels that include certified and professionally approved content (i.e. videos, multimedia, etc.) that expose the three different roles of bully, victim, and bystander, evoking related emotional stimuli detected via user interaction. The user may pass through the three different levels or categories of the content in this example as a game route, and may be asked to identify with one of the three categories. During this exemplary route, the detection phase may monitor the time spent, the way of routing within each level of the virtual reality world, and other user interaction data in order to identify the user's attention and the level of importance the user places on each level and/or selection. The user interaction data from both the calibration phase and the detection phase may be processed to provide the personalized behavior vector that is used to dynamically adjust the virtual reality space that follows in the gamified behavior analysis session. In this way, the particularities of the reaction of each user, in both real world and virtual reality contexts, become structural factors for the gamified environment.

In some examples, biometric features, such as recognition of facial expressions and the ability to infer the likely mental state of other people, are features of social cognition. Analysis of these biometric features may provide a prediction or inference of social capacity beyond traditional neurocognitive assessments that index working memory, psychomotor speed, and attention. Empathy and self-confidence can be associated with biometrics, and levels of each determined from biometric data, in some examples. Biometric data obtained from a wearable device, for example, may be filtered for noise and zero-meaned, then analyzed in time and frequency domains, and features such as High Frequency Fourier Transform (HF_FT) and Difference of Standard Deviations (D_SDT) may be extracted for each signal. In some examples, an algorithm, such as the Kendall Correlation Feature Selection Algorithm, may be used to select only the most important features for classification.

Accelerometer and gyroscope data from a mobile computing device combined with a user position within the virtual reality space may reflect a user route through the gamified virtual reality environment. This information, combined with user interaction data, such as response data to stimuli, forms behavioral features regarding user reaction to specific stimuli, such as content.

In addition, aspects of the disclosure create a model of bullying-related behavior changes, quantified in real life across a population sample. This model is used to extract dynamic evaluations for the current state of an individual concerning empathy and self-confidence. The model is fed by the aforementioned biometrics and behavioral factors and may be realized as a cloud computing machine learning platform, in some examples. The behavioral model may be continuously built and trained to assess the behavioral changes of individual users. This assessment may be expressed as empathy and self-confidence scores, and a Decision Forest classification mechanism may be used in the sequel to produce probabilities and/or severity indices.

Examples of the disclosure may provide one or more computer storage media having computer-executable instructions stored thereon, which, upon execution by a processor, cause the processor to perform operations. These operations may include, for example, without limitation, receiving user interaction data and generating a gamified behavioral analysis session based at least in part on the received user interaction data, dynamically generating a behavioral vector for the gamified behavioral analysis session in response to the received user interaction data, dynamically modifying the gamified behavioral analysis session based at least in part on the dynamically generated behavioral vector and the received user interaction data, storing the gamified behavioral analysis session, including detection moments associated with the gamified behavioral analysis session, using the stored detection moments to generate an augmented reality reflection point, and any other operation within the spirit and scope of this disclosure.

Alternatively, or in addition to the other examples described herein, examples include any combination of the following:
storing session data for the behavior analysis session, including associating a unique identifier with the stored session data;
wherein the user interaction data comprises user input data and biometric data;
wherein the user input includes at least one of interaction data, response data, timing data, attention data, or sensor data;
wherein the biometric data includes at least one of pulse data, temperature data, galvanic skin response data, or gesture detection data;
normalizing the received user interaction data;
extracting features from the normalized user interaction data;
selecting one or more extracted features for classification;
classifying the one or more selected features using a trained behavior model calibrated using the initial calibration prompts during a calibration phase;
generating the dynamic behavior vector for the behavior analysis session, the dynamic behavior vector customized to a user associated with the behavior analysis session;
providing the dynamic behavior vector to a dynamic space modifier, the dynamic space modifier controlling the virtual reality environment;
wherein a content controller provides content to the dynamic space modifier from one or more data sources based at least in part on the dynamic behavior vector;
wherein the dynamic space modifier includes gamification features;
wherein the behavior analysis component is further executed by the processor to generate the virtual reality environment during a calibration phase to calibrate the virtual reality environment to a user and the gamified behavioral analysis session;
generate an augmented reality environment for a computing device using stored detection moments from the gamified behavioral analysis session;
a behavioral analysis session store having a plurality of stored sessions, including stored detection moments associated with an individual stored session and an individual user, the plurality of stored sessions having individual unique identifiers;
wherein the behavior analysis component is further executed by the processor to generate a behavioral vector using the received user interaction data and the trained behavior model, the behavioral vector used to dynamically modify the virtual reality environment;
wherein the behavioral vector includes an empathy value, a self-confidence value, and an awareness value;
wherein the behavior analysis component is further executed by the processor to generate the virtual reality environment during a calibration phase using a collaboration component to calibrate the virtual reality environment to a plurality of users for a gamified multi-player behavioral analysis session;
the virtual reality module storing the gamified behavioral analysis session, including detection moments associated with the gamified behavioral analysis session;
an augmented reality module using the stored detection moments to generate an augmented reality reflection point;

wherein a behavioral analysis back-end aggregates and analyzes stored session data to refine a trained behavior model of the machine learning component;

wherein a computing device obtains individual stored session data using a unique session identifier associated with the individual stored session data.

In some examples, the operations illustrated in FIG. 3 and FIG. 4 may be implemented as software instructions encoded on a computer readable medium, in hardware programmed or designed to perform the operations, or both. For example, aspects of the disclosure may be implemented as a system on a chip or other circuitry including a plurality of interconnected, electrically conductive elements.

While the aspects of the disclosure have been described in terms of various examples with their associated operations, a person skilled in the art would appreciate that a combination of operations from any number of different examples is also within scope of the aspects of the disclosure.

While no personally identifiable information is tracked by aspects of the disclosure, examples have been described with reference to data monitored and/or collected from the users. In some examples, notice may be provided to the users of the collection of the data (e.g., via a dialog box or preference setting) and users are given the opportunity to give or deny consent for the monitoring and/or collection. The consent may take the form of opt-in consent or opt-out consent.

Exemplary Operating Environment

Figure 9:
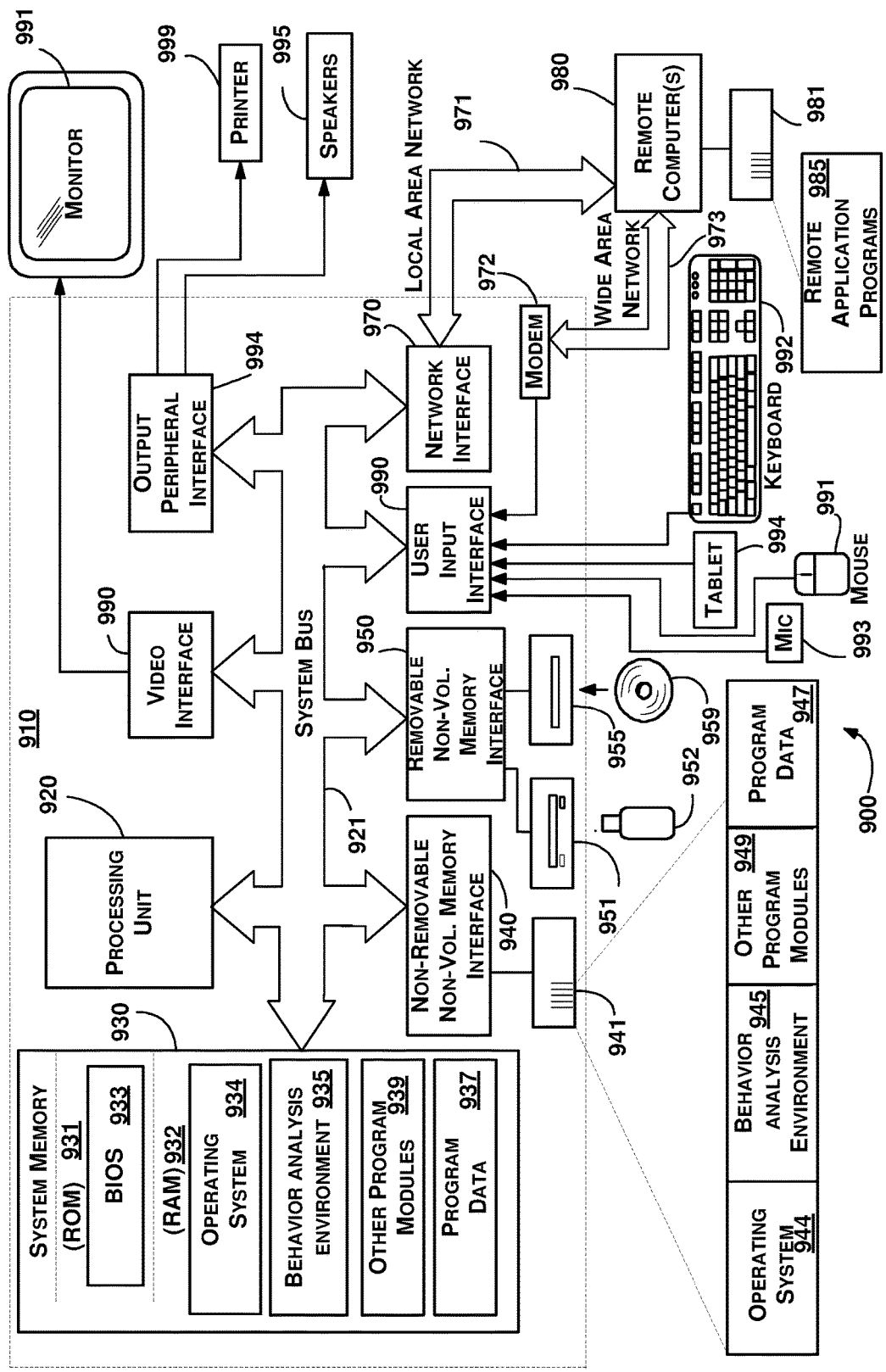
FIG. 9 is an exemplary block diagram illustrating an operating environment for a computing device implementing developer environment.

FIG. 9 illustrates an example of a suitable computing and networking environment 900 on which the examples of FIG. 1 may be implemented. The computing system environment 900 is only one example of a suitable computing environment and is not intended to suggest any limitation as to the scope of use or functionality of the disclosure. Neither should the computing environment 900 be interpreted as having any dependency or requirement relating to any one or combination of components illustrated in the exemplary operating environment 900.

The disclosure is operational with numerous other general purpose or special purpose computing system environments or configurations. Examples of well-known computing systems, environments, and/or configurations that may be suitable for use with the disclosure include, but are not limited to: personal computers, server computers, hand-held or laptop devices, tablet devices, multiprocessor systems, microprocessor-based systems, set top boxes, programmable consumer electronics, network PCs, minicomputers, mainframe computers, distributed computing environments that include any of the above systems or devices, and the like.

The disclosure may be described in the general context of computer-executable instructions, such as program modules, being executed by a computer. Generally, program modules include routines, programs, objects, components, data structures, and so forth, which perform particular tasks or implement particular abstract data types. The disclosure may also be practiced in distributed computing environments where tasks are performed by remote processing devices that are linked through a communications network. In a distributed computing environment, program modules may be located in local and/or remote computer storage media including memory storage devices and/or computer storage devices. As used herein, computer storage devices refer to hardware devices.

With reference to FIG. 9, an exemplary system for implementing various aspects of the disclosure may include a general purpose computing device in the form of a computer 910. Components of the computer 910 may include, but are not limited to, a processing unit 920, a system memory 930, and a system bus 921 that couples various system components including the system memory to the processing unit 920. The system bus 921 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 910 typically includes a variety of computer-readable media. Computer-readable media may be any available media that may be accessed by the computer 910 and includes both volatile and nonvolatile media, and removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, or program modules. Memory 931 and 932 are examples of computer storage media. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by the computer 910. Computer storage media does not, however, include propagated signals. Rather, computer storage media excludes propagated signals. Any such computer storage media may be part of computer 910.

Communication media typically embodies computer-readable instructions, data structures, or program modules in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The system memory 930 includes computer storage media in the form of volatile and/or nonvolatile memory such as read only memory (ROM) 931 and random access memory (RAM) 932. A basic input/output system 933 (BIOS), containing the basic routines that help to transfer information between elements within computer 910, such as during start-up, is typically stored in ROM 931. RAM 932 typically contains data and/or program modules that are immediately accessible to and/or presently being operated on by processing unit 920. By way of example, and not limitation, FIG. 9 illustrates operating system 934, application programs, such as developer environment 935, other program modules 936 and program data 937.

The computer 910 may also include other removable/non-removable, volatile/nonvolatile computer storage media. By way of example only, FIG. 9 illustrates a hard disk drive 941 that reads from or writes to non-removable, nonvolatile magnetic media, a universal serial bus (USB) port 951 that provides for reads from or writes to a removable, nonvolatile memory 952, and an optical disk drive 955 that reads from or writes to a removable, nonvolatile optical disk 956 such as a CD ROM or other optical media. Other removable/non-removable, volatile/nonvolatile computer storage media that may be used in the exemplary operating environment include, but are not limited to, magnetic tape cassettes, flash memory cards, digital versatile disks, digital video tape, solid state RAM, solid state ROM, and the like. The hard disk drive 941 is typically connected to the system bus 921 through a non-removable memory interface such as interface 940, and USB port 951 and optical disk drive 955 are typically connected to the system bus 921 by a removable memory interface, such as interface 950.

The drives and their associated computer storage media, described above and illustrated in FIG. 9, provide storage of computer-readable instructions, data structures, program modules and other data for the computer 910. In FIG. 9, for example, hard disk drive 941 is illustrated as storing operating system 944, behavior analysis environment 945, other program modules 946 and program data 947. Note that these components may either be the same as or different from operating system 934, behavior analysis environment 935, other program modules 936, and program data 937. Operating system 944, behavior analysis environment 945, other program modules 946, and program data 947 are given different numbers herein to illustrate that, at a minimum, they are different copies. A user may enter commands and information into the computer 910 through input devices such as a tablet, or electronic digitizer, 964, a microphone 963, a keyboard 962 and pointing device 961, commonly referred to as mouse, trackball or touch pad. Other input devices not shown in FIG. 9 may include a joystick, game pad, satellite dish, scanner, or the like. These and other input devices are often connected to the processing unit 920 through a user input interface 960 that is coupled to the system bus, but may be connected by other interface and bus structures, such as a parallel port, game port or a universal serial bus (USB). A monitor 991 or other type of display device is also connected to the system bus 921 via an interface, such as a video interface 990. The monitor 991 may also be integrated with a touch-screen panel or the like. Note that the monitor and/or touch screen panel may be physically coupled to a housing in which the computing device is incorporated, such as in a tablet-type personal computer. In addition, computers such as computer 910 may also include other peripheral output devices such as speakers 995 and printer 996, which may be connected through an output peripheral interface 994 or the like.

The computer 910 may operate in a networked environment using logical connections to one or more remote computers, such as a remote computer 980. The remote computer 980 may be a personal computer, a server, a router, a network PC, a peer device or other common network node, and typically includes many or all of the elements described above relative to the computer 910, although only a memory storage device 981 has been illustrated in FIG. 9. The logical connections depicted in FIG. 9 include one or more local area networks (LAN) 971 and one or more wide area networks (WAN) 973, but may also include other networks. Such networking environments are commonplace in offices, enterprise-wide computer networks, intranets and the Internet.

When used in a LAN networking environment, the computer 910 is connected to the LAN 971 through a network interface or adapter 970. When used in a WAN networking environment, the computer 910 typically includes a modem 972 or other means for establishing communications over the WAN 973, such as the Internet. The modem 972, which may be internal or external, may be connected to the system bus 921 via the user input interface 960 or other appropriate mechanism. A wireless networking component such as comprising an interface and antenna may be coupled through a suitable device such as an access point or peer computer to a WAN or LAN. In a networked environment, program modules depicted relative to the computer 910, or portions thereof, may be stored in the remote memory storage device. By way of example, and not limitation, FIG. 9 illustrates remote application programs 985 as residing on memory device 981. It may be appreciated that the network connections shown are exemplary and other means of establishing a communications link between the computers may be used.

The examples illustrated and described herein as well as examples not specifically described herein but within the scope of aspects of the disclosure constitute exemplary means for gamified behavioral analysis in a virtual reality environment. For example, the elements illustrated in FIG. 1 and FIG. 2, such as when encoded to perform the operations illustrated in FIG. 3 and FIG. 4, constitute exemplary means for receiving user interaction data in a virtual reality environment, exemplary means for generating a dynamic behavior vector based on the user interaction data, and exemplary means for dynamically modifying the virtual reality environment using the dynamic behavior vector.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

While the disclosure is susceptible to various modifications and alternative constructions, certain illustrated examples thereof are shown in the drawings and have been described above in detail. It should be understood, however, that there is no intention to limit the disclosure to the specific forms disclosed, but on the contrary, the intention is to cover all modifications, alternative constructions, and equivalents falling within the spirit and scope of the disclosure.

What is claimed is:

1. A method for gamified behavioral analysis, the method comprising:

calibrating, by a processor, a virtual reality environment based on data input in response to initial calibration prompts to provide a customized detection phase for a behavior analysis session;

receiving user interaction data during the customized detection phase;

dynamically pushing the received user interaction data through a trained machine learning component during the customized detection phase to generate a dynamic behavior vector for the behavior analysis session, the dynamic behavior vector updating during the customized detection phase; and dynamically modifying the virtual reality environment during the customized detection phase using the dynamic behavior vector to structure the virtual reality environment.

2. The method of claim 1, further comprising:

storing session data for the behavior analysis session, including associating a unique identifier with the stored session data.

3. The method of claim 1, wherein the user interaction data comprises user input data and biometric data.

4. The method of claim 3, wherein the user input includes at least one of interaction data, response data, timing data, attention data, or sensor data.

5. The method of claim 3, wherein the biometric data includes at least one of pulse data, temperature data, galvanic skin response data, or gesture detection data.

6. The method of claim 1, wherein generating the dynamic behavior vector further comprises:

normalizing the received user interaction data;

extracting features from the normalized user interaction data;

selecting one or more extracted features for classification;

classifying the one or more selected features using a trained behavior model calibrated using the initial calibration prompts during a calibration phase; and generating the dynamic behavior vector for the behavior analysis session, the dynamic behavior vector customized to a user associated with the behavior analysis session.

7. The method of claim 1, wherein dynamically modifying the virtual reality environment during the customized detection phase using the dynamic behavior vector further comprises:

providing the dynamic behavior vector to a dynamic space modifier, the dynamic space modifier controlling the virtual reality environment.

8. The method of claim 7, wherein a content controller provides content to the dynamic space modifier from one or more data sources based at least in part on the dynamic behavior vector.

9. The method of claim 7, wherein the dynamic space modifier includes gamification features.

10. A system for gamified behavioral analysis, the system comprising:

at least one processor, a memory communicatively coupled to the at least one processor, and a behavior analysis component stored on the memory and executed by the processor to:

generate a virtual reality environment for a gamified behavioral analysis session;

receive user interaction data within the virtual reality environment via a wearable device; and dynamically modify the virtual reality environment based on the received user interaction data and a trained behavior model.

11. The system of claim 10, wherein the behavior analysis component is further executed by the processor to generate the virtual reality environment during a calibration phase to calibrate the virtual reality environment to a user and the gamified behavioral analysis session.

12. The system of claim 10, wherein the behavior analysis component is further executed by the processor to:

generate an augmented reality environment for a computing device using stored detection moments from the gamified behavioral analysis session.

13. The system of claim 10, further comprising:

a behavioral analysis session store having a plurality of stored sessions, including stored detection moments associated with an individual stored session and an individual user, the plurality of stored sessions having individual unique identifiers.

14. The system of claim 10, wherein the behavior analysis component is further executed by the processor to generate a behavioral vector using the received user interaction data and the trained behavior model, the behavioral vector used to dynamically modify the virtual reality environment.

15. The system of claim 14, wherein the behavioral vector includes an empathy value, a self-confidence value, and an awareness value.

16. The system of claim 10, wherein the behavior analysis component is further executed by the processor to generate the virtual reality environment during a calibration phase using a collaboration component to calibrate the virtual reality environment to a plurality of users for a gamified multi-player behavioral analysis session.

17. One or more computer storage devices having computer-executable components stored thereon, said components comprising:

a virtual reality module receiving user interaction data and generating a gamified behavioral analysis session based at least in part on the received user interaction data;

a machine learning component dynamically generating a behavioral vector for the gamified behavioral analysis session in response to the received user interaction data; and the virtual reality module dynamically modifying the gamified behavioral analysis session based at least in part on the dynamically generated behavioral vector and the received user interaction data.

18. The one or more computer storage devices of claim 17, having further computer-executable components comprising:

the virtual reality module storing the gamified behavioral analysis session, including detection moments associated with the gamified behavioral analysis session; and an augmented reality module using the stored detection moments to generate an augmented reality reflection point.

19. The one or more computer storage devices of claim 17, wherein a behavioral analysis back-end aggregates and analyzes stored session data to refine a trained behavior model of the machine learning component.

20. The one or more computer storage devices of claim 17, wherein a computing device obtains individual stored session data using a unique session identifier associated with the individual stored session data.

* * * * *